US008592156B2

(12) United States Patent
Liu et al.

(10) Patent No.: US 8,592,156 B2
(45) Date of Patent: Nov. 26, 2013

(54) PREDICTING RESPONSE TO ANTI-CD20 THERAPY IN DLBCL PATIENTS

(75) Inventors: Wei-min Liu, Dublin, CA (US); Yan Li, Palo Alto, CA (US); Chih-Jian Lih, Gaithersburg, MD (US); Yu Chuan Tai, Pleasanton, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 59 days.

(21) Appl. No.: 13/205,469

(22) Filed: Aug. 8, 2011

(65) Prior Publication Data

US 2013/0040831 A1    Feb. 14, 2013

(51) Int. Cl.
 *C12Q 1/68* (2006.01)
(52) U.S. Cl.
 USPC .......................................... 435/6.11; 435/6.1
(58) Field of Classification Search
 None
 See application file for complete search history.

(56) References Cited

U.S. PATENT DOCUMENTS

2003/0219818 A1* 11/2003 Bohen et al. ...................... 435/6
2007/0172847 A1   7/2007 Bonavida et al.

FOREIGN PATENT DOCUMENTS

WO       2009149297 A1   12/2009
WO   PCT/EP2012/003339   10/2012

OTHER PUBLICATIONS

Lenz et al. Stromal gene signatures in Large-B-Cell Lymphomas. The New England Journal of Medicine, vol. 359, No. 22, pp. 2313-2323, Nov. 2008.*
Gutierrez-Garcia et al. Gene-expression profiling and not immunophenotypic algorithms predicts rpognosis in patients with diffuse large B-cell lymphoma treated with immunochemotherapy. Blood, vol. 117, pp. 4836-4843, Mar. 25, 2011.*
Coiffer et al. Rituximab (Anti-CD20 Monoclonal Antibody) for the treatment of patients w ith relapsing or refractory aggressive lymphoma: A multicenter Phase II study. Blood, vol. 92, pp. 1927-1932, Sep. 1998.*
GenBank Accession No. AL576118, GI: 4624900, publicly available Dec. 2010, printed as pp. 1/2 to 2/2 and including p. 1/1 of revision history.*
EST Profile entry for Unigene Hs.655249—mRNA full length insert cDNA clone EUROIMAGE 826033, printed from http://www.ncbi.nlm.nih.gov/UniGene/ESTProfileViewer.cgi?uglist=Hs.655249 on Nov. 30, 2012 as pp. 1/3 to 3/3.*
Coiffer, B., et al., 1998, "Rituximab (Anti-CD20 Monoclonal Antibody) for the Treatment of Patients With Relapsing or Refractory Aggressive Lymphoma: A Multicenter Phase II Study", Blood, 92:1927-1932.
Murawski, Niels, et al., 2010, "Unresolved issues in diffuse large B-cell lymphomas", Expert Rev. Anticancer Ther., 10(3):387-402.
Affymetrix Data Sheet, "Gene Profiling Array cGMP U133 P2", XP007920950, 2011.
Ghosh, Samit, et al., 2011, "Global Gene Expression Profiling of Endothelium Exposed to Heme Reveals an Organ-Specific Induction of Cytoprotective Enzymes in Sickle Cell Disease", PLoS ONE, 6(3):e18398 1-12.
Jais, J-P, et al., 2008, "The expression of 16 genes related to the cell of origin and immune response predicts survival in elderly patients with diffuse large B-cell lymphoma treated with CHOP and rituximab", Leukemia, 22:1917-1924.
Zhang, Meng, et al., 1992, "Cloning and intracellular localization of the U2 small nuclear ribonucleoprotein auxiliary factor small subunit", Proc. Natl. Acad. Sci. USA, 89:8769-8773.
GenBank information for BE858194.1 (accessed on Jan. 22, 2013) showing gene name, 2 pages.
GenBank information for AI763196.1 (accessed on Jan. 22, 2013) showing gene name, 2 pages.
GenBank information for AL576118.3 (accessed on Jan. 22, 2013) showing gene name, 2 pages.
GenBank information for AJ293390.1 (accessed on Jan. 22, 2013) showing gene name, 1 page.
GenBank information for R64696.1 (accessed on Jan. 22, 2013) showing gene name, 2 pages.
GenBank information for AW004885.1 (accessed on Jan. 22, 2013) showing gene name, 1 page.
GenBank information for AI127295.1 (accessed on Jan. 22, 2013) showing gene name, 1 page.
Iqbal, J. et al. Gene expression profiling in lymphoma diagnosis and management. Best Practice & Res Clin. Hematology (2009) 22:191-210.

* cited by examiner

*Primary Examiner* — Jennifer Dunston
(74) *Attorney, Agent, or Firm* — Olga Kay

(57) ABSTRACT

This invention provides methods, compositions, and kits relating to biomarkers whose expression levels are correlated with diffuse large B-cell lymphoma (DLCBL) patients' response to treatment with a CD20 antagonist, such as a CD20 antibody, exemplified by rituximab. The methods, compositions, and kits of the invention can be used to identify DLBCL patients who are likely or not likely, to respond to anti-CD20 treatments.

7 Claims, 5 Drawing Sheets

Kaplan-Meier estimator (p=0.00941)

PREDICTING RESPONSE TO ANTI-CD20 THERAPY IN DLBCL PATIENTS

SEQUENCE LISTING

The instant application contains a Sequence Listing which has been submitted in ASCII format via EFS-Web and is hereby incorporated by reference in its entirety. Said ASCII copy, created on Mar. 12, 2013, is named 27190-US_SL.txt and is 4,534 bytes in size.

BACKGROUND OF THE INVENTION

Lymphoma is the fifth most common cancer in women and the sixth most common cancer in men in the Western world, see Murawski et al. (2010) *Unresolved issues in diffuse large B-cell lymphomas*, Expert Rev. Anticancer Ther. 10(3):387. 90% of aggressive lymphomas originate from B-cells and are classified as diffuse large B-cell lymphomas (DLBCL). Until recently, the accepted form of therapy for DLBCL was CHOP: a combination of cyclophosphamide, hydroxydaunorubicine (doxorubicin), Oncovin® (vincristine) and prednisone. In 1997, the FDA approved rituximab (Rituxan®) for treatment of aggressive Non-Hodgkin lymphomas. Rituximab is a chimeric mouse-human monoclonal antibody against a protein CD20 found primarily on the surface of B-cells. Rituximab has been shown to be effective as a single agent in DLBCL, Coiffier et al. (1998) *Rituximab (anti-CD20 monoclonal antibody) for the treatment of patients with relapsing or refractory aggressive lymphoma: a multicenter Phase II study*. Blood 92(6):1927. Subsequent studies of a combination of rituximab with CHOP demonstrated high response rate with high overall and progression-free survival, even with fewer rounds of CHOP therapy, Murawski et al. (2010), supra. However, it appears that patients receiving rituximab have different response rates, which result in different survival times. Thus, there is a need to identify patients who would benefit from the anti-CD 20 therapy such as rituximab treatment and patients who would likely not respond well to such therapy, and would need a different therapy instead.

SUMMARY OF THE INVENTION

The invention is a method of predicting whether a patient with diffuse large B-cell lymphoma (DLBCL) is likely to exhibit response to anti-CD20 therapy, comprising: obtaining a sample from the patient; determining in the sample the level of expression of one or more genes listed in Table 1 and Table 2; determining whether the patient is likely to exhibit response to anti-CD20 therapy, based on the similarity between the measured level of expression of each gene in the patient's sample and a set of control samples. In some variations of this embodiment, the anti-CD20 therapy comprises an anti-CD20 antibody, for example rituximab.

In another embodiment, the invention is a method of treatment of a diffuse large B-cell lymphoma (DLBCL) patient, comprising: obtaining a sample from the patient; detecting in the sample the expression of one or more genes listed in Table 1 and Table 2; determining whether the patient is likely to exhibit response to anti-CD20 therapy, based on the similarity between the measured expression of each gene measured in the patient's sample and a set of control samples; and administering rituximab if the patient is determined to be likely to respond to anti-CD20 therapy.

In another embodiment, the invention is a set of diagnostic probes for predicting whether a patient with diffuse large B-cell lymphoma (DLBCL) is likely to exhibit response to anti-CD20 therapy, comprising nucleic acid probes or antibodies for detecting expression of one or more genes listed in Table 1 and Table 2.

In another embodiment, the invention is a kit for predicting whether a patient with diffuse large B-cell lymphoma (DLBCL) is likely to exhibit response to anti-CD20 therapy comprising a set of nucleic acid probes for one or more genes listed in Table 1 and Table 2; and reagents necessary for detecting hybridization of the nucleic acid probes. In variations of this embodiment, the kit further comprises antibodies for proteins expressed from the genes listed in Table 1 and Table 2.

DETAILED DESCRIPTION OF THE INVENTION

Definitions

Figure 1:
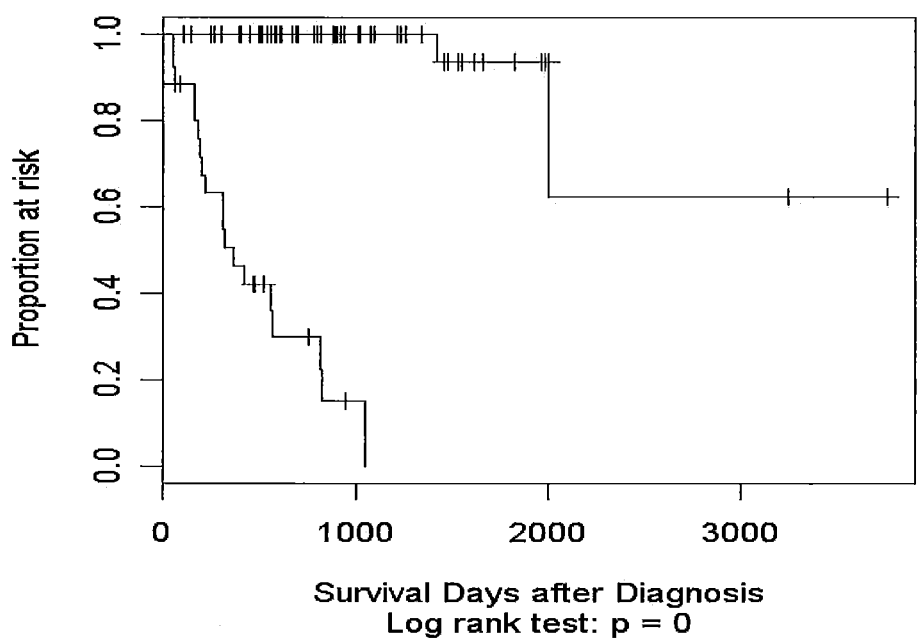
FIG. 1 is a Kaplan-Meier plot showing differences in survival for the model built in Example I validated with re-substitution.

The terms "array," "microarray," and "DNA chip" are used herein interchangeably to refer to an array of distinct polynucleotides affixed to a substrate, such as glass, plastic, paper, nylon, or other type of membrane, filter, chip, or any other suitable solid support. The polynucleotides can be synthesized directly on the substrate, or synthesized separate from the substrate and then affixed to the substrate. Commercial arrays containing probes for all the targets potentially present in a particular type of sample are available. A commercial array may contain probes for all the nucleotide sequences present in the genome. Alternatively, an array may contain probes for only expressed sequences. The term "custom array" refers to an array that contains probes for only selected targets. In the context of the present invention, a custom array may contain probes for some or all of the genes in the expression profile predictive of response to anti-CD20 therapy.

The term "biomarker" refers to a gene or nucleic acid sequence that is of interest for a particular phenotype, such as a disease. For example, a biomarker could be a protein-coding gene whose activation or inactivation leads to a disease. In that case, the presence of the mRNA or the protein could be indicative or predictive of the disease. In another example, a biomarker could be a sequence polymorphism in linkage disequilibrium with an unknown gene causing disease. In that case, the presence of the polymorphism could be indicative or predictive of the disease. In yet another example, a biomarker is a somatic mutation in a gene, wherein the presence of the mutation is correlated with a disease. In that case, the presence of the mRNA mutation could be indicative or predictive of the disease. In the context of the present invention, biomarkers are the genes whose expression (measured by the presence of the mRNA or protein) is in correlation with response or lack of response to anti-CD20 therapy.

The terms "gene expression profile" or "gene expression signature" refer to a collection of expression levels of a number of genes. The genes in the profile are markers that discriminate between individuals with different phenotypes. The discrimination is achieved because the expression levels of each gene exhibit a statistically significant difference among groups of individuals with different phenotypes. Thus each of the phenotypes is characterized by a lowered expression of some genes in the profile, and overexpression of other genes in the profile. By determining the "expression profile," i.e. expression of some or all the genes in the profile, one can assign a phenotype to an individual whose phenotype has not yet manifested itself. In the context of the present invention, by determining the gene expression profile disclosed herein, one can predict a DLBCL patient's response to anti-CD20 therapy.

The term "hybridization" refers to the formation of a duplex between two single-stranded nucleic acids due to complementary base pairing. Hybridization can occur between perfectly complementary nucleic acid strands or between substantially (but not perfectly) complementary nucleic acid strands that contain one or more mismatches. Conditions under which only perfectly complementary nucleic acid strands will hybridize are referred to as "stringent" hybridization conditions. Stable duplexes of substantially complementary nucleic acids can be achieved under less stringent hybridization conditions. Those skilled in the art of nucleic acid technology can determine duplex stability using for example, computer software such as Visual OMP® (DNA Software, Inc., Ann Arbor, Mich.).

The term "primer" refers to an oligonucleotide that acts as a point of initiation of DNA synthesis under suitable conditions in the presence of nucleic acid precursors and an agent for polymerization. A primer can either consist entirely of the target-hybridizing region or can contain additional features which allow for detection, immobilization, or manipulation of the amplified product.

The term "probe" refers to a nucleic acid that selectively hybridizes to a target nucleic acid under suitable conditions. A probe can either consist entirely of the target-hybridizing region or can contain additional features which allow for the detection, immobilization, or manipulation of the probe-target duplex. The probe may contain modifications to its primary structure by the addition of labels, linkers, peptides or any other groups necessary to perform the detection assay in the chosen format.

The term "probe set" refers to a unique set of oligonucleotides in a microarray capable of detecting a marker. Typically, a microarray contains several probe sets for detecting each marker or gene. In commercial microarrays, each probe set is associated with a sequence that is searchable in a public database by a unique accession number.

The terms "target sequence" or "target" refer to a region of a nucleic acid that is to be analyzed.

The terms "nucleic acid," "polynucleotide" and "oligonucleotide" refer to target sequences, primers and probes. The terms are not limited by length and are generic to linear polymers of deoxyribonucleotides (single-stranded or double-stranded DNA), ribonucleotides (RNA), and any other N-glycoside of a purine or pyrimidine base, including adenosine, guanosine, cytidine, thymidine and uridine and modifications of these bases.

The term "response to therapy" refers to a benefit attributable to therapy. Response may be assessed by measuring a clinically relevant parameter, such as tumor shrinkage, length of overall survival or survival without disease progression. For example, the clinically relevant parameter may be the length of survival following the start of the therapy. The patient who has survived for a certain time, e.g. at least three years, may be considered to have responded to therapy. The patient, who has not survived past three years, is considered to not have responded or responded poorly to therapy.

The term "sample" refers to any composition containing or presumed to contain nucleic acid. This includes a sample of tissue or fluid isolated from an individual for example, skin, plasma, serum, spinal fluid, lymph fluid, synovial fluid, urine, tears, blood cells, organs and tumors, including the fresh-frozen tissue and formalin-fixed paraffin embedded tissue (FFPET), and also to samples of in vitro cultures established from cells taken from an individual, and nucleic acids isolated therefrom.

The term "training set" or "control set" refers to a set of samples used to establish a correlation between two variables. For example, a training set is a set of patient samples used to establish a correlation between the expression of a gene and the patient's condition. In the context of the present invention, the training set is a set of samples from DLBCL patients receiving anti-CD20 therapy, for whom survival information is available. The training set is used to establish a correlation between the expression profile and survival.

The term "testing set" refers to a set of samples used to verify the correlation established using the training set. For example, a testing set is a set of samples from patients for whom both gene expression and the patient's condition are known. This set is used to verify whether the correlation established using the training set will correctly predict the patient's condition. In the context of the present invention, the testing set is an independent set of samples from DLBCL patients receiving anti-CD20 therapy, for whom survival information is available. The testing set is used to measure expression of the genes in the profile and test whether the actual survival data matches the prediction made by measuring the gene expression.

The term "test sample" refers to a patient's sample that is to be tested for a particular parameter.

The present invention is based on the discovery that expression of certain genes predicts response of diffuse large B-cell lymphoma (DLBCL) patients to anti-CD20 therapy. Specifically, it was discovered that some genes exhibit differential expression between a group of DLBCL patients with response to rituximab therapy and patients with poor response to rituximab therapy, where the response is measured by the length of survival following the therapy. The invention comprises such genes and gene expression profiles containing such genes. The invention further comprises the use of the genes and gene expression profiles to predict response of DLBCL patients to anti-CD20 therapy.

The genes identified as differentially expressed in responders and poor responders to anti-CD20 therapy among DLBCL patients are listed in Tables 1 and 2. In Tables 1 and 2, the column "PS ID" lists the identification code for the probe set in the Affymetrix GeneChip® Human Genome U133 Plus 2.0 Array (Affymetrix, Santa Clara, Calif.) The column "NCBI" lists the corresponding public reference number (NCBI Accession No.). The column "Gene Title" lists the names of the genes, where available. The column "Gene Symbol" lists the gene symbols, where available. The column "p-value" in Table 1 lists the p-value statistic. The column "FDR_BH" in Table 2 lists the values of the statistic False Discovery Rate (FDR), calculated according to the method described in Benjamini Y. and Hochberg, Y., (1995) J Royal Stat. Soc. Ser. B 57:289.

TABLE 1

Predictive markers identified in Example 1

| PS ID | NCBI | Symbol | Gene Title | p-value |
|---|---|---|---|---|
| 202858_at | NM_006758 | U2AF1 | U2 small nuclear RNA auxiliary factor 1 | 8.40E−05 |
| 205215_at | NM_007212 | RNF2 | ring finger protein 2 | 4.10E−05 |
| 205877_s_at | NM_017590 | ZC3H7B | zinc finger CCCH-type containing 7B | 4.10E−05 |
| 208656_s_at | AF135162 | CCNI | cyclin I | 1.90E−05 |
| 208776_at | BF432873 | PSMD11 | proteasome (prosome, macropain) 26S subunit, non-ATPase, 11 | 6.00E−05 |
| 210461_s_at | BC002448 | ABLIM1 | actin binding LIM protein 1 | 3.50E−05 |
| 210964_s_at | U94364 | GYG2 | glycogenin 2 | 6.20E−05 |
| 212669_at | AI093569 | CAMK2G | calcium/calmodulin-dependent protein kinase (CaM kinase) II gamma | 6.70E−06 |
| 212678_at | AW054826 | NF1 | neurofibromin 1 (neurofibromatosis, von Recklinghausen disease, Watson disease) | 3.40E−05 |
| 213658_at | BE858194 | SEQ ID NO: 1 | mRNA full length insert cDNA clone EUROIMAGE 826033 | 3.70E−08 |
| 213748_at | AW271713 | TRIM66 | tripartite motif-containing 66 | 3.30E−05 |
| 214891_at | U79257 | FBXO21 | F-box protein 21 | 4.90E−05 |
| 218205_s_at | NM_017572 | MKNK2 | MAP kinase interacting serine/threonine kinase 2 | 6.50E−05 |
| 224642_at | BG291550 | FYTTD1 | forty-two-three domain containing 1 | 7.70E−05 |
| 224808_s_at | AI090768 | GET4 | Golgi to ER traffic protein 4 homolog | 7.80E−05 |
| 226004_at | AI910855 | CABLES2 | Cdk5 and Abl enzyme substrate 2 | 3.60E−05 |
| 227844_at | AI089932 | FMNL3 | formin-like 3 | 2.50E−05 |
| 230566_at | AI806805 | C22orf27 | chromosome 22 open reading frame 27 | 6.70E−05 |
| 231997_at | R69910 | TBCEL | tubulin folding cofactor E-like | 6.90E−05 |
| 232076_at | AW294133 | ZNF707 | zinc finger protein 707 | 3.60E−05 |
| 235640_at | AI763196 | SEQ ID NO: 2 | transcribed locus | 7.80E−05 |
| 236449_at | AI885390 | CSTB | cystatin B (stefin B) | 2.70E−05 |
| 236604_at | BF195603 | BAHCC1 | BAH domain and coiled-coil containing 1 | 2.00E−05 |
| 239656_at | AA827176 | LOC723809 | hypothetical LOC723809 | 6.90E−05 |
| 240377_at | AI344289 | NPIP | nuclear pore complex interacting protein | 3.40E−05 |
| 241388_at | AL567118 | — | cDNA FLJ40566 fis, clone THYMU2004733 | 1.40E−05 |
| 243518_at | BF195694 | LOC730367 | hypothetical protein LOC730367 | 1.10E−05 |
| 1553326_at | AF453828 | RXFP2 | relaxin/insulin-like family peptide receptor 2 | 3.70E−05 |
| 1554732_at | BC020886 | MGC24125 | hypothetical protein MGC24125 | 2.40E−05 |
| 1566337_x_at | AJ293390 | SEQ ID NO: 3 | mRNA, differentially expressed in malignant melanoma, clone MM A2 | 5.80E−05 |

TABLE 2

Predictive markers identified in Example 2

| PS ID | NCBI | Gene Title | Symbol | FDR_BH |
|---|---|---|---|---|
| 200730_s_at | BF576710 | protein tyrosine phosphatase type IVA, member 1 | PTP4A1 | 1.79E−07 |
| 201800_s_at | AF185696 | oxysterol binding protein | OSBP | 1.79E−07 |
| 213359_at | W74620 | heterogeneous nuclear ribonucleo-protein D (AU-rich element RNA binding protein 1, 37 kDa) | HNRNPD | 1.79E−07 |
| 200848_at | AA479488 | adenosylhomocysteinase-like 1 | AHCYL1 | 2.45E−07 |
| 37170_at | AB015331 | BMP2 inducible kinase | BMP2K | 3.00E−07 |
| 202438_x_at | BF346014 | iduronate 2-sulfatase | IDS | 6.15E−07 |
| 242814_at | AI986192 | serpin peptidase inhibitor, clade B (ovalbumin), member 9 | SERPINB9 | 6.15E−07 |
| 233396_s_at | AK023759 | CSRP2 binding protein | CSRP2BP | 8.81E−07 |
| 211744_s_at | BC005930 | CD58 molecule | CD58 | 8.98E−07 |
| 233509_at | AK021844 | hect domain and RLD 4 | HERC4 | 8.98E−07 |
| 210093_s_at | AF067173 | mago-nashi homolog, proliferation-associated (*Drosophila*) | MAGOH | 1.24E−06 |
| 223892_s_at | AF182414 | transmembrane BAX inhibitor motif containing 4 | TMBIM4 | 1.60E−06 |
| 243361_at | N51597 | splicing factor, arginine/serine-rich 12 | SFRS12 | 2.02E−06 |
| 216252_x_at | Z70519 | Fas (TNF receptor superfamily, member 6) | FAS | 2.68E−06 |
| 231369_at | BG149482 | Zinc finger protein 333 | ZNF333 | 2.68E−06 |
| 243267_x_at | AI127295 | SEQ ID NO: 4 | — | 2.79E−06 |
| 1555063_at | BC029495 | ubiquitin specific peptidase 6 (Tre-2 oncogene) | USP6 | 3.39E−06 |
| 225026_at | BF572029 | chromodomain helicase DNA binding protein 6 | CHD6 | 4.47E−06 |
| 236246_x_at | BF195670 | hypothetical protein LOC653160 | LOC653160 | 4.47E−06 |
| 243931_at | R64696 | SEQ ID NO: 5 | — | 4.47E−06 |

TABLE 2-continued

Predictive markers identified in Example 2

| PS ID | NCBI | Gene Title | Symbol | FDR_BH |
|---|---|---|---|---|
| 200918_s_at | NM 003139 | signal recognition particle receptor (docking protein) | SRPR | 5.19E−06 |
| 215719_x_at | X83493 | Fas (TNF receptor superfamily, member 6) | FAS | 5.33E−06 |
| 224917_at | BF674052 | microRNA 21 | MIR21 | 5.33E−06 |
| 225173_at | BE501862 | Rho GTPase activating protein 18 | ARHGAP18 | 5.33E−06 |
| 239387_at | AW004885 | SEQ ID NO: 6 | — | 5.33E−06 |
| 238549_at | AI420611 | core-binding factor, runt domain, alpha subunit 2; translocated to 2 | CBFA2T2 | 5.77E−06 |
| 201150_s_at | NM 000362 | TIMP metallopeptidase inhibitor 3 | TIMP3 | 6.02E−06 |
| 218924_s_at | NM004388 | di-N-acetyl-chitobiase | CTBS | 6.92E−06 |
| 228822_s_at | AI435036 | ubiquitin specific peptidase 16 | USP16 | 7.26E−06 |
| 210621_s_at | M23612 | RAS p21 protein activator (GTPase activating protein) 1 | RASA1 | 7.69E−06 |
| 229961_x_at | AI871270 | YjeF N-terminal domain containing -3 | YJEFN3 | 8.19E−06 |

Measuring expression of one or more of the genes in the profile allows predicting whether a DLBCL patient is, or is not likely to respond to anti-CD20 therapy, such as for example, rituximab. In the context of the present invention, measuring the level of expression of a gene in a patient's sample may be accomplished by several means. Gene expression may eb measured by measuring the level of RNA expressed by the gene. The amount of RNA may be determined for example, by reverse transcription followed by quantitative PCR (qPCR) amplification. Gene expression may also be detected by hybridizing a single probe to the RNA in a blot or hybridizing the RNA to multiple probes in an array and quantifying the hybridization signal. Alternatively, expression of protein-coding gene can be determined by measuring the level of expression of the protein encoded by the gene or measuring enzymatic activity of the expressed protein consisting in part or entirely of the protein encoded by the gene. As an additional alternative, it is possible to indirectly assess the expression of a gene listed in Table 1 or Table 2 by measuring the level of expression or activity of a gene or protein situated downstream in a biological pathway from any gene listed in Table 1 or Table 2. For such downstream pathway gene or protein, the expression may also be measured at various levels, including the nucleic acid level, protein level, and activity level.

To predict likelihood of a DLBCL patient's response to anti-CD20 therapy, expression of at least one, more than one or all of the genes listed in Tables 1 and 2 may be measured. A person skilled in the art of statistics would recognize that a smaller subset of genes among those listed in Tables 1 and 2 may be sufficient to predict a patient's response. For example, a subset of genes may be selected based on the value of the T-statistic, the p-value or the FDR value. A person skilled in the art is aware of the statistical methods for selecting a subset of genes from an expression profile. For example, the smallest number of genes that is sufficient to predict response may be determined by calculating the area under the curve of the receiver operating characteristic ("AUC of RUC" method) as described in Green, D. M., Swets, J. A., (1966) *Signal detection theory and psychophysics*, Wiley, N.Y.; Swets, J. A., Pickett, R. M. (1982) *Evaluation of diagnostic systems: Methods from signal detection theory*, Academic Press, New York; and Pepe, M. S. (2003), *The statistical evaluation of medical tests for classification and prediction*, Oxford Univ. Press.

Additional genes may be added to the profile predictive of a DLBCL patient's response to anti-CD20 therapy, as long as expression of the genes differs between the patients who respond and patients who do not respond to anti-CD20 therapy. For example, when measuring the difference in expression, the p-value or the FDR value may be used to select additional genes to be added to the profile.

In the examples of the expression profiles of the present invention, the expression of each gene was measured in a first set of patient samples whose response (or lack of response) to anti-CD20 therapy has been documented. This first set of samples (referred to as the training set) contained an adequate number of responder patients and an adequate number of non-responder patients.

To predict response to anti-CD20 therapy in a patient, the expression profile in the patient's tumor sample was determined and compared to the expression profile in the samples of the training set. A statistical model was used to determine whether based on the expression profile, the patient is likely to belong to a responder group or a non-responder group for the anti-CD20 therapy. In the method of the present invention, the gene expression in the test sample and the samples of the training set need not be measured simultaneously. For convenience, expression data from the training set samples may be stored on a computer readable medium and accessed each time a new patient sample is tested.

Response Prediction

In one embodiment, the invention comprises a method of predicting response of a DLBCL patient to anti-CD20 therapy, such as rituximab. The method comprises obtaining a tumor sample from a patient diagnosed with DLBCL and measuring expression level of one or more genes listed in Tables 1 and 2 prior to the patient receiving the therapy and comparing the expression to the expression of the same genes in the samples of the training set.

The expression levels of any gene listed in Tables 1 and 2 may be measured for example, by measuring the level of mRNA expressed from the gene in the patient's sample by reverse transcription and quantitative PCR (qPCR) amplification of the resulting cDNA, see U.S. Pat. Nos. 5,210,015 and 5,487,972 and Holland et al. (1991) PNAS USA 88: 7276. For multiple genes, the levels of mRNA may be measured in a microarray-based assay. For example, multiple mRNA molecules can be reverse-transcribed using common poly-A primers, converted into cDNA and then into labeled amplified RNA (aRNA) that is applied to an array of immobilized probes. (MAQC Consortium (2006) Nat Biotechnol. 24(9):1151-61). The expression may be detected using commercially available microarrays, for example from Roche NimbleGen, Inc. (Madison, Wisc.) or Affymetrix, Inc. (Santa Clara, Calif.). Alternatively, only selected probe sets for each of the genes listed in Tables 1 and 2 may be used. The sequences of probes corresponding to each gene are listed in the literature accompanying the Affymetrix GeneChip® Human Genome U133 Plus 2.0 Array product. A person skilled in the art of nucleic acid hybridization may also design custom hybridization probes for the genes listed in Tables 1 and 2 using the gene sequences available through the public databases. A person skilled in the art of nucleic acid arrays may also design a custom array containing previously known or custom designed probes for one or more, or all the genes listed in Tables 1 and 2 according to *DNA Microarrays: A Molecular Cloning Manual*, (2003), Eds. Bowtell and Sambrook, Cold Spring Harbor Laboratory Press.

Any alternative methods of amplifying and quantifying mRNA or cDNA may also be used in the context of the present invention. Furthermore, as an alternative to detecting gene transcripts on the nucleic acid level, the protein products of the genes in Tables 1 and 2 may be detected, where the protein products are present. The proteins may be detected, for example, by immunoassays. In another variation of this embodiment, the mRNA transcripts or protein products of genes that are linked to the genes in Tables 1 and 2 by a biological pathway, may be detected instead of (or in addition to) detecting the mRNA transcripts or proteins corresponding to the genes in Tables 1 and 2.

After the expression level of one or more genes from Tables 1 and 2 has been determined in the patient's sample, the expression is compared to the documented expression of the same gene or genes in the set of samples taken from patients whose response anti-CD20 therapy (e.g. rituximab) has been documented (training set). A statistical tool is then used to determine whether the test patient will respond to anti-CD20 therapy such as rituximab. For example, to determine whether the patient is classified in the responder group or a non-responder group, the Support Vector Machine (SVM) method (Cortes, C. and Vapnik, V. (1995) Machine Learning, 20:273-297) or the k-nearest neighbor method described e.g. in Hastie et al., (2001) *The Elements of Statistical Learning: Data Mining, Inference, and Prediction*, Springer, N.Y., may be used.

Method of Treatment

In another embodiment, the invention is a method of treatment of DLBCL. The method comprises collecting a tumor sample from a patient diagnosed with DLBCL and measuring the level of expression of one or more genes from Tables 1 and 2 in the sample. In variations of this embodiment, mRNA levels or levels of the protein products of the genes from Tables 1 and 2 may be detected. In another variation of this embodiment, the transcripts or protein products of genes that are linked to the genes in Tables 1 and 2 by a biological pathway may be detected instead of (or in addition to) detecting the transcripts or proteins corresponding to the genes in Tables 1 and 2.

After the expression level of one or more genes from Tables 1 and 2 has been determined in the patient's sample, the expression is compared to the expression of the same gene or genes in samples of patients whose response to anti-CD20 therapy has been documented. A statistical tool is then used to determine whether the test patient will likely respond to anti-CD20 therapy. If the patient is predicted to respond to anti-CD20 therapy, the therapy (e.g. an antibody such as rituximab) is administered alone or in combination with additional therapeutic agents.

Gene Expression Profile

In another embodiment, the invention comprises a set of detection probes for predicting response of DLBCL patients to anti-CD20 therapy (e.g. rituximab). The detection probes may comprise nucleic acid probes for detecting expression of the genes listed in Table 1, or Table 2, or both. The exact sequence of each nucleic acid probe is not critical. A person skilled in the art of nucleic acid hybridization will be able to select a probe or probes for detecting expression of each gene based on the published sequence, and assemble the set of probes according to the present invention. For example, for each gene listed in Table 1 or Table 2, the probes listed in the product literature for the Affymetrix GeneChip® Human Genome U133 Plus 2.0 Array may be used to assemble the set of probes according to the present invention.

In some embodiments, detection probes other than nucleic acid probes may be used. For example, antibodies may be used to detect the presence of proteins that are encoded by the genes listed in Table 1 or Table 2, where such proteins are available. In some embodiments, probes or antibodies for the genes linked to the genes listed in Table 1 or Table 2 in a biological pathway may also be included. Thus in some embodiments of the invention, the set of detection probes includes nucleic acid probes, antibodies, or a combination of both.

Kits

In another embodiment, the invention is a kit for predicting response to anti-CD20 therapy in a DLBCL patient. An exemplary kit comprises probes that detect expression of at least one, two or all of the genes listed in Tables 1 and 2. The kit may comprise additional reagents necessary to extract and amplify RNA from the patient's sample. In variations of this embodiment, the kit comprises a set of oligonucleotide probes that detect expression of at least one, two or all of the genes set forth in Tables 1 and 2, attached to a solid support, such as a microarray slide or chip. The kit may also contain reference material, e.g. samples from patients whose response to anti-CD20 therapy, for example, rituximab, has been documented.

In some embodiments of the invention, the kit may contain antibodies for detecting proteins that are encoded by the genes set forth in Tables 1 and 2. In some embodiments, probes or antibodies for the genes linked to the genes listed in Table 1 or Table 2 in a biological pathway may also be included. The kit may comprise additional reagents for antibody-based detection of proteins.

EXAMPLES

Example 1

Selecting Predictive Expression Markers in DLBCL Patients Treated with Rituximab Using the Cox Proportional Hazards Model and a K-Nearest-Neighbor Method Tumor samples were obtained from DLBCL patients undergoing therapy with CHOP-R (CHOP in combination with rituximab). For these patients, the three-year survival status has been documented. The samples underwent gene expression profiling through use of an Affymetrix GeneChip® Human Genome U133 Plus 2.0 Array (Affymetrix, Inc. Santa Clara, Calif.). Applying a quality control, samples with low signals or less than 18% present calls (microarray signals) were eliminated. The resulting pool consisted of 85 patients falling into two groups: Group 1—21 long-term survivors, with survival greater than three years (1095 days) and Group 2—19 short term survivors, who died prior the end of three years and 45 patients who dropped out prior to the end of three years.

The microarray expression data was analyzed using the Cox proportional hazards model (Cox, D. R. (1972) *Regression models and life tables*, J R Statistical Soc. Ser., 34:187-220, Lachin, J. M. (2000) *Biostatistical Methods: The Assessment of Relative Risks*, Wiley, N.Y.). For each gene, the Cox model was used to test association between the level of expression of the gene and survival past three years. Based on the value of the T-statistic, the Cox model selected 200 genes. Of the 200 genes, 30 genes with the lowest p-value (Table 1) were selected for the model.

Next, the 1-nearest neighbor method (a version of the k-nearest neighbor method with k=1 (T. Hastie et al., (2001) *The Elements of Statistical Learning: Data Mining, Inference, and Prediction*, Springer, N.Y.)), was used to group patients according to the gene expression. The model was tested with two methods of cross-validation.

The first validation was performed using the re-substitution method. The accuracy of re-substitution validation was 90%. Results of the re-substitution validation are shown on FIG. 1. FIG. 1 is a Kaplan-Meier plot (Kaplan, E. L. and Meier, P. (1958) J. Amer. Stat. Assn. 53:457) demonstrating the difference in survival between the two groups selected according to the model. The upper curve represents the actual survival data for patients predicted to be respondents, while the lower curve represents the actual survival data for patients predicted to be non-respondents by the method of the present invention.

Figure 2:
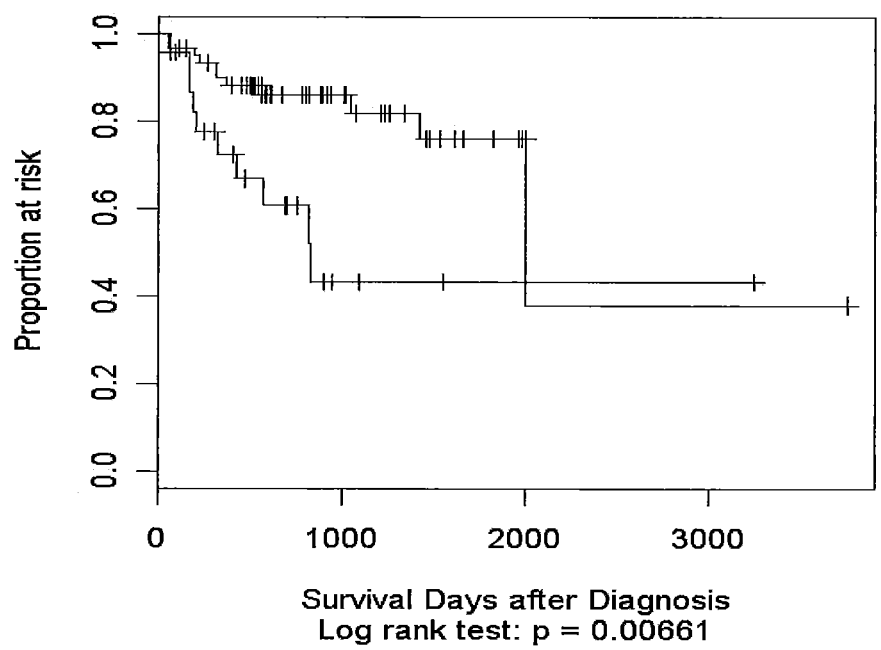
FIG. 2 is a Kaplan-Meier plot showing differences in survival for leave-one-out cross validation of the model built in Example 1.

The second validation was performed using the leave-one-out cross validation method. The accuracy of leave-one-out cross-validation was 72%. Results of the leave-one-out cross validation are shown on FIG. 2. FIG. 2 is a Kaplan-Meier plot demonstrating the difference in survival between the two groups selected according to the model. The upper curve represents the actual survival data for patients predicted to be respondents, while the lower curve represents the actual survival data for patients predicted to be non-respondents by the method of the present invention.

Example 2

Selecting Predictive Expression Markers in DLBCL Patients Treated with Rituximab Using the Cox Proportional Hazards Model and Support Vector Machine Method Tumor samples were obtained from DLBCL patients undergoing therapy with CHOP and patients undergoing CHOP-R (CHOP in combination with rituximab) therapy. 159 patients for whom the three-year survival status has been documented were selected. Samples from patients who left the study prior to the end of the three year period were not used in this example.

The 159 samples were randomly split into a training and a testing set in three separate runs as follows: Run 1: 75 training, 84 testing; Run 2: 78 training, 81 testing; Run 3: 83 training, 76 testing. The samples underwent gene expression profiling through use of an Affymetrix GeneChip® Human Genome U133 Plus 2.0 Array.

The microarray expression data was analyzed using the Cox proportional hazards model. For each gene, the Cox model was used to test association between the level of expression and survival past three years. The Cox model was applied to the three testing sets (Runs 1, 2 and 3). The genes with the lowest False Discovery Rate (FDR) were selected. The FDR cut-off of 0.01 yielded 31 genes (Table 2). These 31 genes were selected for model building and cross-validation.

To predict patient's survival past three years, the Support Vector Machine (SVM) method (Cortes, C. and Vapnik, V. (1995) Machine Learning, 20:273-297) was used. SVM is a binary classifier that classifies an input into one of the two classes based on the input data. SVM was applied to classify patient samples into Group 1 (survival more than three years) or Group 2 (survival less than three years) based on the expression levels of the 31 genes in Table 2.

Figure 3:
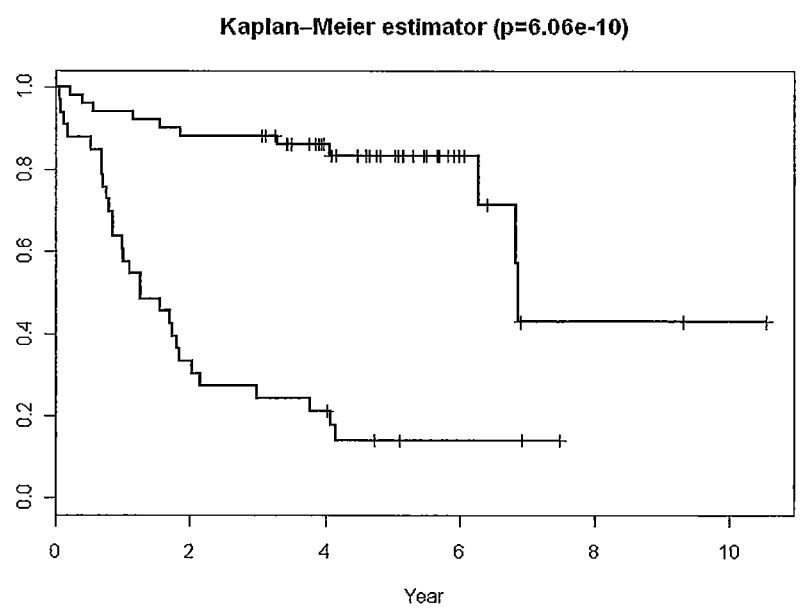
FIG. 3 is a Kaplan-Meier plot constructed with the classification according to the SVM method for the model built in Example 2.

After the samples were separated into Group 1 and Group 2 using the SVM method, a Kaplan-Meier plot was assembled (FIG. 3). Group 1 contained 51 samples and Group 2 contained 33 samples. The upper curve represents the actual survival data for patients predicted to be respondents, while the lower curve represents the actual survival data for patients predicted to be non-respondents by the method of the present invention. The Log Rank test was used to determine whether the two curves (for Group 1 and Group 2) were significantly different. Log Rank test yielded a highly significant p-value of $6.06 \times 10^{-10}$.

Figure 4:
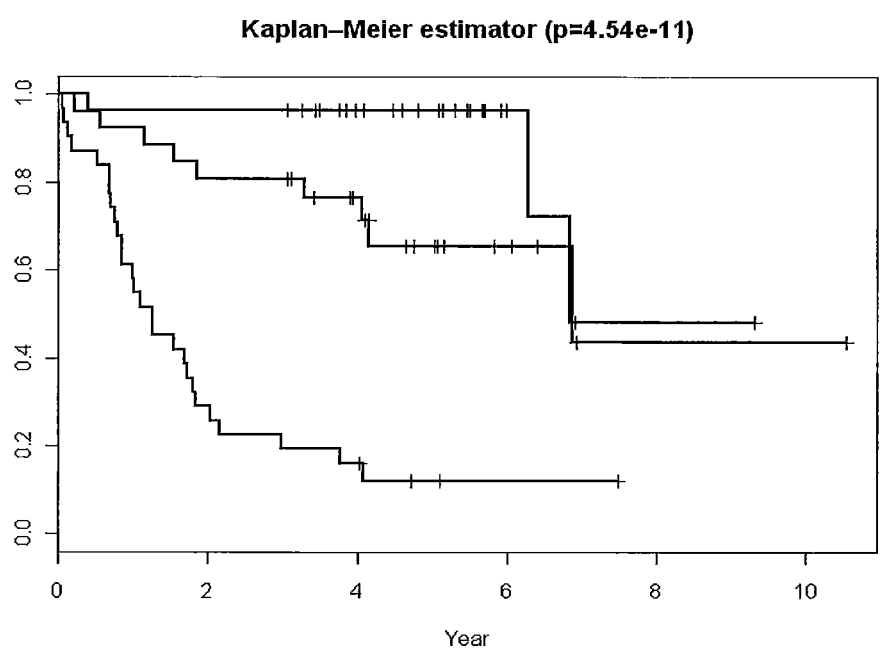
FIG. 4 is a Kaplan-Meier plot constructed with the probability assigned according to the SVM method for the model built in Example 2.

Alternatively, SVM was used to determine the probability that a sample belongs to one of the two groups. This approach yields three classifications: Group 1, Group 2 and unclassified samples for whom the probability of belonging to either group is less than 90%. After the samples were separated into Group 1 and Group 2 using the SVM method, a Kaplan-Meier plot was assembled (FIG. 4). Group 1 contained 27 samples, Group 2 contained 31 samples and the remaining 26 samples were unclassified. Log Rank test yielded a highly significant p-value of $4.54 \times 10^{-11}$. FIG. 4 shows the Kaplan-Meier plot for the 84 samples from the testing set in Run 1. The upper curve represents the actual survival data for patients predicted to be respondents, while the lower curve represents the actual survival data for patients predicted to be non-respondents by the method of the present invention. The middle curve represents the actual survival data for the unclassified group.

Example 3

Validating the Model on DLBCL Patients Treated with Rituximab

Figure 5:
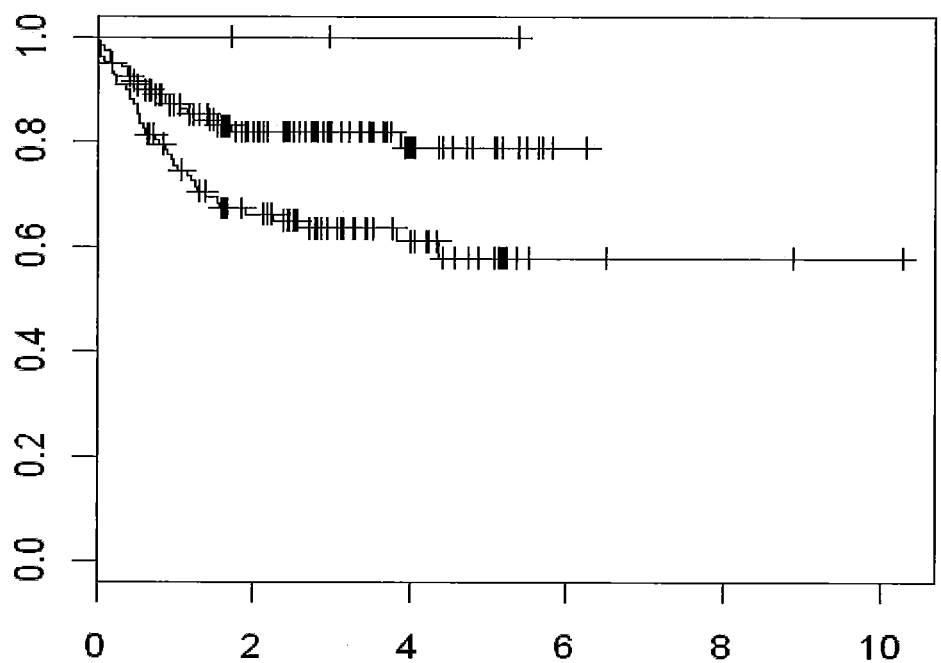
FIG. 5 is a Kaplan-Meier plot showing differences in survival for the independent set of samples in Example 3.

The method was applied to an independent set of samples: 233 tumor samples from DLBCL patients on the CHOP-R therapy for whom survival data was available. SVM was used to determine the probability of each patient belonging to Group 1 (survival more than three years) or Group 2 (survival less than three years). Samples with low probability of belonging to either group remained unclassified. After the samples were separated into Group 1 and Group 2 using the SVM method, a Kaplan-Meier plot was assembled using the survival information available for each sample (FIG. 5). The middle curve represents the actual survival data for patients predicted to be respondents, while the lower curve represents the actual survival data for the unclassified patients. The upper curve represents the actual survival data for patients predicted to be non-respondents by the method of the present invention. The data does not contradict the teachings of the invention. The upper curve represents only three patients, all of whom left the study prior to the expiration of the three-year period (at 1.71, 2.95 and 5.37 years). Unfortunately, although the curve shows a 100% survival, the censored patients may have passed away within the three-year period.

While the invention has been described in detail with reference to specific examples, it will be apparent to one skilled in the art that various modifications can be made within the scope of this invention. Thus the scope of the invention should not be limited by the examples described herein, but by the claims presented below.

What is claimed is:

1. A method of assessing a patient with diffuse large B-cell lymphoma (DLBCL), comprising:
   (a) obtaining a sample of the patient's tumor; and
   (b) determining in the sample the level of expression of a gene combination consisting of U2AF1, RNF2, ZC3H7B, CCNI, PSMD11, ABLIM1, GYG2, CAMK2G, NF1, SEQ ID NO: 1, TRIM66, FBXO21, MKNK2, FYTTD1, GET4, CABLES2, FMNL3, C22orf27, TBCEL, ZNF707, SEQ ID NO: 2, CSTB, BAHCC1, LOC723809, NPIP, gene coding for cDNA FLJ40566 fis clone THYMU2004733, LOC730367, RXFP2, MGC24125, SEQ ID NO: 3, PTP4A1, OSBP, HNRNPD, AHCYL1, BMP2K, IDS, SERPINB9, CSRP2BP, CD58, HERC4, MAGOH, TMBIM4, SFRS12, FAS, ZNF333, SEQ ID NO: 4, USP6, CHD6, LOC653160, SEQ ID NO: 5, SRPR, MIR21, ARHGAP18, SEQ ID NO:6, CBFA2T2, TIMP3, CTBS, USP16, RASA1 and YJEFN3.

2. The method of claim 1, wherein the patient is a candidate for anti-CD20 therapy.

3. The method of claim 2, wherein the anti-CD20 therapy is rituximab.

4. The method of claim 1, wherein the expression of the genes is measured by measuring the level of RNA transcribed from each gene.

5. The method of claim 1, further comprising determining the level of expression of the genes listed in step (b) in a control set of samples comprising a representative number of patients that exhibit response to anti-CD20 therapy and a representative number of patients that exhibit no response or poor response to anti-CD20 therapy.

6. The method of claim 1, wherein the level of expression is assessed using statistical methods.

7. A method of selecting a diffuse large B-cell lymphoma (DLBCL) patient for treatment with rituximab, comprising:
   (a) obtaining a sample of the patient's tumor;
   (b) detecting in the sample the expression of a gene combination consisting of U2AF1, RNF2, ZC3H7B, CCNI, PSMD11, ABLIM1, GYG2, CAMK2G, NF1, SEQ ID NO: 1, TRIM66, FBXO21, MKNK2, FYTTD1, GET4, CABLES2, FMNL3, C22orf27, TBCEL, ZNF707, SEQ ID NO: 2, CSTB, BAHCC1, LOC723809, NPIP, gene coding for cDNA FLJ40566 fis clone THYMU2004733, LOC730367, RXFP2, MGC24125, SEQ ID NO: 3, PTP4A1, OSBP, HNRNPD, AHCYL1, BMP2K, IDS, SERPINB9, CSRP2BP, CD58, HERC4, MAGOH, TMBIM4, SFRS12, FAS, ZNF333, SEQ ID NO: 4, USP6, CHD6, LOC653160, SEQ ID NO: 5, SRPR, MIR21, ARHGAP18, SEQ ID NO: 6, CBFA2T2, TIMP3, CTBS, USP16, RASA1 and YJEFN3;
   (c) comparing the expression determined in step (b) to the expression of the same genes in a control set of samples comprising a representative number of patients that exhibit response to rituximab therapy and a representative number of patients that exhibit no response or poor response to rituximab therapy to determine if the patient is likely to respond to rituximab; and
   (d) administering rituximab if the patient is determined likely to respond to rituximab.

* * * * *

SEQUENCE LISTING

<160> NUMBER OF SEQ ID NOS: 6

<210> SEQ ID NO 1
<211> LENGTH: 553
<212> TYPE: DNA
<213> ORGANISM: Homo sapiens

<400> SEQUENCE: 1

```
aataaaaatc ataactaaca tttattgagt gctaactgtg tgccaggcct ttattaactc      60
atgtgatcct caaagcgatg ttggctctgt cattgtcatc gttttacaga tgcagaaact     120
gaagaacaga gaacttagat agctcatgca agatgacaac acagcaggag gtgacagaca    180
ctttatttcg ttaccgtgag ataatatttc aaataagtgt atgggaaaga aagttagaaa    240
ggggaaaaaa tggcagccgg aaagataagg gagagccagg tgaggtccca actccaagta    300
caccatggga ggtcctaagc aagggacatg cagaggggag atctgagctt cccagcaacc    360
aaggcaaaaa agtgtcaatc agtcacactc ttcacaagtg cctgccagag actataaccc    420
acatactcat gaaagggcca gacagccctg acgttaagat ctgggagaaa ttttaggaga    480
ggatcctatg cctcagcagt tcgtagaagt ttcagaggct gtcagaaaac atcccaagtg    540
ttagcggtag cct                                                        553
```

<210> SEQ ID NO 2
<211> LENGTH: 341
<212> TYPE: DNA
<213> ORGANISM: Homo sapiens
<220> FEATURE:
<221> NAME/KEY: modified_base
<222> LOCATION: (32)..(32)
<223> OTHER INFORMATION: a, c, t, g, unknown or other

<400> SEQUENCE: 2

```
tttttttttt tttttttaaa atcattaaat tncatttat tttcattttg ccctttattt      60
tttcattttt tagttgtgaa agtagttcgt atatatttag aaaaatgttt acttttaata    120
aactattcat ttaataaatg tattaactga gcactaaata atgctcaaag gatcatagat    180 tttttttcctc cacactaagc ccatgggaca tgaagaatat ctgggtgctt ccaggatatt    240
aagtaggaat gtgccttttc ccactcctgg cctttgggta ctgtcctgag catgggatgc    300
tggggcaggg gctgccttgg ccatcttgcc atctgcatgg c                        341
```

<210> SEQ ID NO 3
<211> LENGTH: 294
<212> TYPE: DNA
<213> ORGANISM: Homo sapiens

<400> SEQUENCE: 3

```
tcgagcggcc gcccgggcag gtactctgcg ttgttaccac tgcttacgcg tgttctgcgt      60
tgttaccact gcttcccgcg tactctgcgt tgttaccact gcttcccgcg tactctgcgt    120
tgttaccact gcttacgcgt actctgcgtt gttaccactg cttacgcgta ctctgcgttg    180
ttaccactgc ttacgcgaac tctgcgttgt taccgctgct tacgcgtact ctgcgttgtt    240
accactgctt acgcgtactc tgcgttgtta ccactgcttc ccgcgtacct cggc          294
```

<210> SEQ ID NO 4
<211> LENGTH: 485
<212> TYPE: DNA
<213> ORGANISM: Homo sapiens

<400> SEQUENCE: 4

| | | | | | |
|---|---|---|---|---|---|
| tttttagtg | tatttttcgt | ggttggatca | aaaagacttg | agttttaat | ttaatttatt | 60 |
| ccctgccgtt | gtagcggggc | ggggtccctg | tgccctggcc | tggggagggg | aacgcggaa | 120 |
| catggggtcg | ggaacacagc | cgctcccctc | tgctctgcac | cccactcgtg | ggggaacaca | 180 |
| gccgctcccc | tctgctctgc | accccactcg | tgggggaaca | cagccgctcc | cctctgctct | 240 |
| gcaccccact | cgtgggggaa | cacagccgct | cccctctgct | ctgcaccca | ctcgtggggg | 300 |
| aacacagctg | cagcccaccg | cggacccccc | tggtgctcca | ggttgggtga | gtctgagccg | 360 |
| gaagggggtac | gtggtgggcg | ccctcattg | tggctgggga | gaccttatac | cccatcgccc | 420 |
| accccgtcc | tcctggtcat | ttcctcccag | acactgtttt | gccccagcgc | cttcggaat | 480 |
| cacag | | | | | 485 |

<210> SEQ ID NO 5
<211> LENGTH: 448
<212> TYPE: DNA
<213> ORGANISM: Homo sapiens
<220> FEATURE:
<221> NAME/KEY: modified_base
<222> LOCATION: (379)..(379)
<223> OTHER INFORMATION: a, c, t, g, unknown or other
<220> FEATURE:
<221> NAME/KEY: modified_base
<222> LOCATION: (396)..(396)
<223> OTHER INFORMATION: a, c, t, g, unknown or other

<400> SEQUENCE: 5

| | | | | | |
|---|---|---|---|---|---|
| gtggcactga | gtttccatag | aacttcaaaa | caattggttg | atttcactta | aaaaaaaaa | 60 |
| aaaaagtcat | tcaatataca | gaaaattact | ccctggtca | gtactgttag | ccccagataa | 120 |
| tctgaaaaaa | tttgttctta | aaaaaaaaaa | acaatttgga | ggccaggcat | ggtggctcat | 180 |
| gcctgtaatc | ccagcacatt | gagaggtcga | gttgtgtgca | tcacttgagc | ccagggagtt | 240 |
| tgagaccagc | ctgggacaac | atggtgaaac | actatctcta | caagaaaata | caaaaattag | 300 |
| ccagggcatg | gtggtgcatg | cctgttagtc | ccagctactc | aggaggctga | ggcgggaggg | 360 |
| gaggcagatg | ttgccagtna | gctgaggttg | ttgccnctgc | attcccgcct | ggggttatgg | 420 |
| gagttagacc | ctgttttaa | aaaaacaa | | | 448 |

<210> SEQ ID NO 6
<211> LENGTH: 448
<212> TYPE: DNA
<213> ORGANISM: Homo sapiens

<400> SEQUENCE: 6

| | | | | | |
|---|---|---|---|---|---|
| aaatgaaaaa | ctaacttggg | aaatacattc | tttgatgggg | ctagccacac | atatgtttta | 60 |
| caatacttgg | tctgcaatgc | tgtcttttgg | gtctgagttt | cttctcagga | gggtatcttt | 120 |
| gggccagcaa | taacaatcat | tgttcagtta | tacaaactt | ataatttctg | aagtaatttc | 180 |
| ctatacatca | tttcacttaa | tctttacaaa | aaccctatag | agaaagcagg | gtaaagtctg | 240 |

-continued

```
aaataataaa taataatcag ttaatggaaa tagagtatct acatcctgga aatgatggct    300
atgttataca ctatgctagc tctagacatt cttgtatgtg gatgaaatta gcttcaatac    360
aaccatatga acagattggg tccagaggca gagggaggca cacacagatc atttgacttg    420
cgtgcttcag atgaggaaac acgcatag                                       448
```